(12) United States Patent
Moor et al.

(10) Patent No.: US 8,772,579 B2
(45) Date of Patent: Jul. 8, 2014

(54) LETTUCE VARIETY EMERSON

(75) Inventors: Cornelis Marinus Moor, Monster (NL); Egbert Carolus Johannes Smits, Zevenbergen (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 840 days.

(21) Appl. No.: 12/408,007

(22) Filed: Mar. 20, 2009

(65) Prior Publication Data

US 2010/0229255 A1 Sep. 9, 2010

Related U.S. Application Data

(60) Provisional application No. 61/158,078, filed on Mar. 6, 2009.

(51) Int. Cl.
| | |
|---|---|
| *A01H 1/00* | (2006.01) |
| *A01H 4/00* | (2006.01) |
| *A01H 5/00* | (2006.01) |
| *A01H 5/10* | (2006.01) |
| *A01H 5/12* | (2006.01) |
| *C12N 15/82* | (2006.01) |

(52) U.S. Cl.
USPC ........... 800/305; 800/260; 800/278; 435/410; 435/430

(58) Field of Classification Search
None
See application file for complete search history.

(56) References Cited

U.S. PATENT DOCUMENTS 6,320,104 B1 * 11/2001 Moor et al. ............. 800/305
7,790,962 B2 * 9/2010 Moor et al. ............. 800/305

OTHER PUBLICATIONS

Lebeda et al, Chapter 9, Genetic Resources, Chromosome Engineering and Crop Improvement, vol. 3, Vegetable Crops, Singh, editor, 2007, CRC Press, pp. 378-472.*
Jeuken and Lindhout, abstract P289, Plant && Animal Genome VII Conference, San Diego, CA, Jan. 17-19, 1999.*
IBEB press release "New race of *Bremia lactucae* BI:27 identified and nominated", May 2010; Plantum NL (Dutch association for breeding, tissue culture, production and trade . . . .
Michelmore R. & Ochoa. O. "Breeding Crisphead Lettuce."In: California Lettuce Research Board, Annual Report 2005-2006, 2006, Salinas, California, pp. 55-68.
Schettini, T.M., Legg, E.J., Michelmore, R.W., 1991. Insensitivity to metalaxyl in California populations of *Bremia lactucae* and resistance of California lettuce cultivars . . . .
Van Ettekoven, K. et al., "Identification and denomination of 'new' races of *Bremia lactucae*," In: Lebeda, A. and Kristkova, E (eds.), Eucarpia Leafy Vegetables, 1999 . . . .
Van der Arend et al. "Identification and denomination of "new" races of *Bremia lactucae* in Europe by IBEB until 2002." In: Van Hintum, Th et al. (eds.), Eucarpia Leafy . . . .

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to a new lettuce (*Lactuca sativa*) variety, seed designated as 79-11 RZ, which exhibits a combination of an extraordinary high number of leaves, resistance to many *Bremia*-races, and an extraordinary low number of apices under many growing conditions, the representative seed having been deposited with the National Collections of Industrial, Marine and Food Bacteria (NCIMB) in Bucksburn, Aberdeen AB21 9YA, Scotland, UK and assigned NCIMB Accession No. 41614, The present invention also relates to a *Lactuca sativa* plant produced by growing the 79-11 RZ (Emerson) seed. The invention further relates to methods for producing the lettuce cultivar, represented by lettuce variety 79-11 RZ.

25 Claims, No Drawings

LETTUCE VARIETY EMERSON

This application claims priority to U.S. provisional patent application Ser. No. 61/158,078 filed Mar. 6, 2009.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a new lettuce (*Lactuca sativa*) variety, which exhibits a combination of an extraordinary high number of leaves, resistance to many *Bremia lactucae* Regal strains, and an extraordinary low number of apices under many growing conditions.

BACKGROUND OF THE INVENTION

All cultivated forms of lettuce belong to the highly polymorphic species *Lactuca sativa* that is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, dandelion, artichoke and chrysanthemum. Sativa is one of about 300 species in the genus *Lactuca*.

Lettuce cultivars are susceptible to a number of diseases such as downy mildew, sclerotinia rot, botrytis, powdery mildew, anthracnose, bottom rot, corky root rot, lettuce mosaic virus, big vein, beet western yellows and aster yellows. These diseases result in millions of dollars of lost lettuce crop throughout the world every year.

Of the various diseases that affect lettuce cultivars, downy mildew (*Bremia lactucae*) is the most highly destructive of lettuce grown at relatively low temperature and high humidity. Downy mildew is caused by an oomycete, *Bremia lactucae* Regal, which can be one of the following strains: Bl:18, Bl:20, Bl:22, Bl:24, Bl:25, Bl:26 (Van Ettekoven, K. et al., "Identification and denomination of 'new' strains of *Bremia lactucae*." In: Lebeda, A. and Kristkova, E (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151), Ca-VII, Ca-VIII (Michelmore R. & Ochoa. O. "Breeding Crisphead Lettuce." In: California Lettuce Research Board, Annual Report 2005-2006, 2006, Salinas, Calif., pp. 55-68), NL341, and NL519. NL341 (IBEB sextet-code EU-A 55-63-13-01) and NL519 (IBEB sextet-code EU-A 27-63-13-01) were selected, because they are widely occurring in Europe since 2005, and because they are breaking the well-known dm17-gene, which was considered to provide broad resistance to lettuce downy mildew (Van der Arend et al. 1999 & 2003; Michelmore & Ochoa, 2006).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the pathogen progresses to this degree, the head cannot be harvested. Less severe damage requires the removal of more leaves than usual, especially when the lettuce reaches its final destination.

Although several known lettuce cultivars exhibit resistance against downy mildew, irrespective of lettuce type, all the lettuce cultivars affected produce a limited number of leaves that generally are of unequal size and diminished quality with respect to color and shape. This is a distinct disadvantage for processing purposes because leaves either need to be sorted based on size or they need to be cut to a smaller, more uniform size. The first option requires additional labor, with not all sizes usable. The second option has the disadvantage that it creates many cut surfaces, which then are subject to wound-induced browning, resulting in a greatly reduced shelf-life.

Although green lettuce plants exist that have a large number of small, more uniform leaves (U.S. Pat. No. 6,320,104; US patent application 20070022496), they all lack resistance to newly appearing lettuce downy mildew strains, like the ones mentioned above: Bl:18, Bl:20, Bl:22, Bl:24, Bl:25, Bl:26, Ca-VII, Ca-VIII, NL341, NL519.

Another undesired feature of existing green lettuce plants that have a large number of small, more uniform leaves (U.S. Pat. No. 6,320,104; US patent application 20070022496), is that they show multiple apices in warm growing conditions with sufficient moisture available. In these conditions the apex is splitting up in several independent apices. An example of such warm growing conditions can be a daytime temperature of 30° C. and a night time temperature of 20° C. at a day length of 14 hours. If these multiple apices appear in an early growing stage it makes the plant unsuitable for marketing as wholehead, and much less suitable for harvesting single leaves. If these multiple apices appear in a later growing stage, it makes the plants less marketable as wholehead. Those plants can still be used for single leaf harvesting.

A need exists, therefore, for an improved green lettuce variety, which exhibits resistance to downy mildew and exhibits abundant leaf growth without multiple apices.

Citation or identification of any document in this application is not an admission that such document is available as prior art to the present invention.

SUMMARY OF THE INVENTION

The present invention provides a new type of lettuce (*Lactuca sativa*) variety, designated 79-11 RZ and referred to as Emerson. Lettuce cultivar 79-11 RZ exhibits a combination of resistance to downy mildew (*Bremia lactucae* Regal) strains NL1, NL2, NL4, NL5, NL6, NL7, NL10, NL12, NL13, NL14, NL15, NL16, Bl:17, Bl:18, Bl:20, Bl:21, Bl:22, Bl:23, Bl:24, Bl:25, Bl:26, Ca-I, Ca-II, Ca-III, Ca-IV, Ca-V, Ca-VI, Ca-VII, Ca-VIII, NL519 and NL341, as well as an extraordinary high number of uniformly sized, green, round-shaped leaves, as well as an extraordinary low number of apices under many warm growing conditions as compared to other existing lettuce varieties. Seeds of lettuce cultivar 79-11 RZ were deposited on Mar. 2, 2009 with the National Collections of Industrial, Marine and Food Bacteria (NCIMB) in Bucksburn, Aberdeen AB21 9YA, Scotland, UK and have been assigned NCIMB Accession No. 41614. Deposited seed will be irrevocably and without restriction or condition released to the public during the term of any patent issued from this application.

The present invention also provides parts of the plant of lettuce cultivar 79-11 RZ that are suitable for sexual reproduction, including but not limited to microspores, pollen, ovaries, ovules, embryo sacs or egg cells.

The present invention further provides parts of the plant of lettuce cultivar 79-11 RZ that are suitable for vegetative reproduction, including but not limited to cuttings, roots, stems, cells or protoplasts, leaves, meristems or buds.

The present invention still further provides a tissue culture from lettuce cultivar 79-11 RZ in which the tissue culture is derived from a tissue including but not limited to leaves, pollen, embryos, cotyledon, hypocotyls, meristematic cells, roots, root tips, anthers, flowers, seeds or stems.

The present invention also provides a plant grown from the seeds, regenerated from the above-described plant parts, or regenerated from the above-described tissue culture, having all of the morphological and physiological characteristics of lettuce cultivar 79-11 RZ.

The present invention further provides progeny of lettuce cultivar 79-11 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-11 RZ.

The present invention still further provides a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-11 RZ.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The Deposits with National Collections of Industrial, Marine and Food Bacteria (NCIMB) in Bucksburn, Aberdeen AB21 9YA, Scotland, UK, under deposit accession number NCIMB Accession No. 41614 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

DETAILED DESCRIPTION

The present invention provides a new type of lettuce (*Lactuca sativa*) variety, designated 79-11 RZ and referred to as Emerson. Lettuce cultivar 79-11 RZ exhibits a combination of resistance to downy mildew (*Bremia lactucae* Regal) strains NL1, NL2, NL4, NL5, NL6, NL7, NL10, NL12, NL13, NL14, NL15, NL16, Bl:17, Bl:18, Bl:20, Bl:21, Bl:22, Bl:23, Bl:24, Bl:25, Bl:26, Ca-I, Ca-II, Ca-III, Ca-IV, Ca-V, Ca-VI, Ca-VII, Ca-VIII, NL519 and NL341, as well as an extraordinary high number of uniformly sized, green, round-shaped leaves, as well as a significantly reduced number of apices under many warm growing conditions. Seeds of lettuce cultivar 79-11 RZ were deposited on Mar. 2, 2009 with the National Collections of Industrial, Marine and Food Bacteria (NCIMB) in Bucksburn, Aberdeen AB21 9YA, Scotland, UK and have been assigned NCIMB Accession No. 41614.

As used herein, resistance to *Bremia lactucae* Regal is defined as the capacity of a plant to resist infection by each of the aforementioned strains of the *Bremia lactucae* Regal in all stages between the seedling stage and the harvestable plant stage.

Resistance typically is tested by two interchangeable methods, as described by Bonnier, F. J. M. et al. (Euphytica, 61(3):203-211, 1992). One method involves inoculating 7-day old seedlings and observing sporulation 10 to 14 days later. The other method involves inoculating leaf discs with a diameter of 18 mm obtained from a non-senescent, fully grown true leaf and observing sporulation 10 days later.

As used herein, an extraordinary high leaf number is the leaf number of a lettuce plant which is at least about two times to about four times as high as the leaf number of a plant of a regular lettuce variety grown in the same environment during the same period of time. The observation of leaf number should be done at the plant stage where the above-ground dry matter is between 100 and 400 grams and before the plant starts to bolt.

As used herein, a multileaf lettuce plant is a lettuce plant with an extraordinary high leaf number. This is caused by a single recessive genetic factor, which is present in the plant in a homozygous state.

As used herein, harvest maturity is the stage of the lettuce plant at which the lettuce plant is ready for harvest for human consumption. In the case of green lettuce with the multileaf characteristic harvest maturity is defined by a fresh weight of the above-ground part of the plant between 200 and 300 grams.

As used herein, a warm environment is characterized by an average temperature between 15° Celsius and 25° Celsius, and by an average number of apices at harvest maturity between 2 and 4 for a multileaf lettuce plant of the cultivar "Socrates", grown under these conditions.

As used herein, an extraordinary low number of apices is the number of apices of a multileaf lettuce plant which is at least about one times to three times lower that the apices number of a plant of a known multileaf lettuce variety, like "Socrates", grown in the same warm environment during the same period of time.

As used herein, an acceptable product for consumers and/or the lettuce processing industry is defined as the absence of tipburn, short core and an extraordinary high number of relatively uniform-sized, green, round-shaped lettuce leaves.

In an embodiment of the present invention, there also is provided parts of the plant of lettuce cultivar 79-11 RZ that are suitable for sexual reproduction, which include, without limitation, microspores, pollen, ovaries, ovules, embryo sacs or egg cells.

In another embodiment, there is provided parts of the plant of lettuce cultivar 79-11 RZ that are suitable for vegetative reproduction, which include, without limitation, cuttings, roots, stems, cells, protoplasts, leaves, meristems or buds.

In a further embodiment, there is provided a tissue culture from lettuce cultivar 79-11 RZ in which the tissue culture is derived from a tissue such as, for example and without limitation, leaves, pollen, embryos, cotyledon, hypocotyls, meristematic cells, roots, root tips, anthers, flowers, seeds or stems.

In still a further embodiment, there is provided a plant grown from the seeds, regenerated from the above-described plant parts, or regenerated from the above-described tissue culture, having all of the morphological and physiological characteristics of lettuce cultivar 79-11 RZ.

In still another embodiment, there is provided progeny of lettuce cultivar 79-11 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-11 RZ. Progeny of the lettuce cultivar 79-11 RZ can be modified in one or more other characteristics, in which the modification is a result of, for example and without limitation, mutagenesis or transformation with a transgene.

In still a further embodiment, there is provided a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-11 RZ.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

In general, selection is first practiced among $F_2$ plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

The characteristic of lettuce having an extraordinary high leaf number is caused by a single genetic factor, which is introduced via crossing with a multileaf plant and then selecting for the distinct group of descendants with a higher leaf number than the contrasting group of descendants with a lower leaf number (U.S. Pat. No. 6,320,104). These distinct groups easily can be recognized in an $F_2$-population from a single cross between a multileaf lettuce plant and a plant of a regular lettuce variety without an extraordinary high leaf number by a cumulative frequency distribution graph of leaf number per plant, which can be supported by statistical analysis based on mixture models.

Based on a likelihood ratio test, it can be shown that a bimodal distribution supports the observed distribution of plant leaf numbers much better than a unimodal distribution. The number of plants belonging to the two distinguishable groups, i.e., high leaf number and low leaf number, follows a typical Mendelian segregation ratio of 1:3, indicating a single recessive genetic factor for the high leaf number trait. The observation that the ratio between the two group sizes follows a 1:3 segregation ratio can be supported statistically by a chi-square test.

The present invention is more particularly described in the following non-limiting example, which is intended to be illustrative only, as numerous modifications and variations therein will be apparent to those skilled in the art.

The invention will now be further described by way of the following non-limiting example.

Example 1

Development and Characteristics of Lettuce Cultivar 79-11 RZ

The breeding history of the lettuce cultivar of the present invention was as follows. In 2001, the breeding of "Emerson" began with a cross between an $F_5$-plant "01S.2062" and a BC3-S2-plant "01D.6003". Plant "01S.2062" was derived by inbreeding from the same cross as from which the cultivar "Socrates" was derived, but was not part of the pedigree of "Socrates". It was homozygous for the Dm16-gene for *Bremia*-resistance, while Socrates has the Dm18-gene. Plant "01D.6003" was derived by inbreeding from a BC3-backcross using the iceberg cultivar "Salinas" as backcross parent and a plant of the species *Lactuca saligna* as a donor parent of *Bremia* resistance.

After two cycles of inbreeding and selection for *Bremia*-resistance and the multileaf characteristic, an $F_3$-plant was selected and numbered "03S.173". In January 2003 it was used as a father plant in a cross with a plant of the F8-line "03S.23424" as a mother. This line was derived by inbreeding from the same cross as from which the cultivar "Socrates" was derived, but was not part of the pedigree of "Socrates". It was homozygous for the Dm16-gene for *Bremia*-resistance, while Socrates has the Dm18-gene.

An $F_1$-plant "01S.602103" of the newly made cross was used as a father in a cross with another plant of the F8-line "03S.23424" as a mother. The cross was made in summer 2003 and an F1-seed designated "03S.96475" was directly sown and brought to flowering in a glasshouse in Fijnaart, the Netherlands, to produce an $F_2$-seed, designated "04S.23294", which was sown in January 2004 in a spring glasshouse trial in 's-Gravenzande, The Netherlands.

In April, 2004, an $F_2$-plant was selected for having an extraordinary high leaf number and having *Bremia* resistance to strain Bl:20. The $F_2$-plant produced $F_3$-seed, designated "05S.13599", which was sown in an autumn glasshouse trial in De Lier, The Netherlands. In October, 2004, it was observed in this trial that the $F_3$-seed produced plants with an extraordinary high leaf number, resulting in a harvestable product acceptable for consumers. At this time, an $F_3$-plant was selected from the trial as having an extraordinary high leaf number and having *Bremia* resistance to strains Bl:20 and Bl:24. The $F_3$-plant produced $F_4$-seed, designated "05S.16109", which was sown in a spring glasshouse trial in De Lier, The Netherlands. In May, 2005, it was observed in this trial that the $F_4$-seed produced plants with an extraordinary high leaf number, resulting in a harvestable product acceptable for consumers.

At this time, an $F_4$-plant was selected from the trial as having an extraordinary high leaf number. The $F_4$-plant produced $F_5$-seed, designated "06S.19566", which was sown in an outdoor spring trial in Aramon, France. In April, 2006, it was observed in this trial that the $F_5$-seed produced plants with an extraordinary high leaf number, resulting in a harvestable product acceptable for consumers. At this time, an $F_5$-plant was selected from the trial as having an extraordinary high leaf number. The $F_5$-plant produced $F_6$-seed, designated "06P.85447", which was sown in an outdoor autumn trial in Aramon, France. In October, 2006, it was observed in this trial that the $F_6$-seed produced plants with an extraordinary high leaf number, resulting in a harvestable product acceptable for consumers. At this time, an $F_6$-plant was selected from the trial as having an extraordinary high leaf number and a remarkably low number of apices.

In 2007, the $F_7$-plant produced $F_7$-seed, designated "07P.76874", which was uniformly resistant against downy mildew (*Bremia lactucae*) strain Bl:21, and NL341. Based on several confidential trials performed in 2007 and 2008, the $F_7$-seed also was uniform for type, field performance, bolting and sensitivity for tipburn.

In the spring of 2007, the $F_7$-seed was used to sow a multiplication in Hoek van Holland, The Netherlands. The progeny of this multiplication showed phenotypical uniformity during seed production and seed was harvested for further trials. In several confidential trials conducted in 2008, the multiplied seed, designated by the introduction number 79-11 RZ, displayed a harvested product which had the characteristics acceptable by the lettuce processing industry and/or consumers. Seeds of 79-11 RZ, referred to as "Emerson", were deposited on Mar. 2, 2009 with the National Collections of Industrial, Marine and Food Bacteria (NCIMB) in Bucksburn, Aberdeen AB21 9YA, Scotland, UK and have been assigned NCIMB Accession No. 41614.

The multiplied seed of "Emerson" was used for seedling tests against *Bremia lactucae* Regal. Resistance to the following strains was observed: Bl:16, Bl:17, Bl:18, Bl:20, Bl:21, Bl:22, Bl:23, Bl:24, Bl:25, Bl:26, Ca-VII, Ca-VIII, NL341, and NL519. No susceptibility was observed against any of the tested strains of *Bremia lactucae* Regal.

"Emerson" was compared to "Socrates" and proved to be different on several aspects. "Emerson" has black seeds, while "Socrates" has white seeds. This difference in seed color of cultivated lettuce is determined by a single gene. "Emerson" is resistant against the *Bremia lactucae* Regal strains: Bl:18, Bl:20, Bl:22, Bl:24, Bl:25, Bl:26, Ca-VII, Ca-VIII, NL341, and NL519, while "Socrates" is susceptible. This is determined by a single resistance gene, which has been obtained from the *Lactuca saligna* plant in the pedigree of "Emerson". Two other black-seeded candidate varieties, "07R.7980" and "05R.5504", showed resistance against *Bremia lactucae* Regal strains Bl:18, Bl:20, Bl:22, Bl:24, Bl:25, Bl:26, Ca-VII, Ca-VIII, but were susceptible for *Bremia lactucae* Regal strains NL341 and NL519. "Emerson" showed significantly less multiple apices than "Socrates" in two trials in warm conditions (see Table 1). Statistical testing was performed by an F-test after analysis of variance, using location and cultivar as explanatory factor, and the P-value was 0.0015. Comparison between "Emerson" and two other candidate varieties also showed significantly less multiple apices in "Emerson" The P-values for the F-test were 0.0052 and 0.0092, for comparisons of "Emerson" with "07R.7980" and "05R.5504", respectively.

TABLE 1

Observed number of apices per plant at mature plant stage. Observations of 10 plants per cultivar per location. Cultivars and candidate-cultivars: "Emerson", "Socrates", "07R.7980", "05R.5504".
Locations: Glasshouse De Lier (sowing Aug. 24, 2007; transplanting Sep. 6, 2007; observation Oct. 24, 2007), Glasshouse Fijnaart (sowing Jul. 11, 2008; transplanting Jul. 25, 2008; observation Sep. 2, 2008)

| Trial Location | "Emerson" | "Socrates" | 07R.7980 | 05R.5504 |
| --- | --- | --- | --- | --- |
| Glasshouse De Lier | 1, 1, 2, 1, 2, 1, 2, 1, 1, 1 | 3, 1, 1, 4, 1, 3, 2, 2, 3, 1 | 1, 2, 3, 1, 1, 1, 2, 1, 3, 3 | 2, 1, 2, 3, 1, 4, 2, 1, 1, 2 |
| Glasshouse Fijnaart | 2, 1, 2, 3, 2, 1, 1, 2, 1, 3 | 1, 4, 2, 3, 4, 3, 3, 3, 4, 2 | 3, 3, 5, 3, 2, 2, 2, 3, 2, 3 | 3, 2, 4, 2, 2, 3, 2, 4, 4, 1 |

The distinctive resistance characteristics of the lettuce cultivar 79-11 RZ seeds and plants of the present invention provides a significant advantage for growers trying to grow lettuce with many uniformly-sized leaves without the attendant high costs due to *Bremia* attacks. *Bremia* resistance prevents the "Emerson" plant from getting infected by downy mildew—the most prevalent disease of lettuce. Due to the *Bremia* resistance of the "Emerson" plant, the need for a number of costly fungicidial sprays is reduced.

This has the advantage of alleviating consumers' concerns about fungicide residues on their lettuce due to the reduction or absence of fungicide applications on the lettuce crops. Additionally, the *Bremia* resistance provided by the "Emerson" seeds and plants of the present invention decreases the number of harvest losses, resulting in a higher yield per unit area. Furthermore, the multileaf characteristic, i.e., extraordinary high number of leaves on a single lettuce plant, of the "Emerson" plant, provides the salad industry with a product that is very suitable for processing—after cutting the leaves from the main core of the lettuce head, no further sorting or cutting is required to produce an edible salad. This reduces the costs of bagged salad production and results in less labor and/or increased shelf life.

Additionally, under warm conditions, "Emerson" is showing significantly less multiple apices than "Socrates", which is providing a higher percentage marketable heads to the grower. This increases the grower's income per hectare.

The invention is further described by the following numbered paragraphs:

1. A lettuce plant designated 79-11 RZ, referred to as Emerson, representative seed of which having been deposited under NCIMB Accession No. 41614, wherein said plant has
(a) an extraordinary high number of green, round-shaped leaves;
(b) an extraordinary low number of apices; and
(c) resistance to downy mildew.

2. A seed of the plant of claim 1.

3. A part of the plant of claim 1, wherein said part of the plant is suitable for sexual reproduction.

4. The part of the plant of claim 3, wherein said part is selected from the group consisting of microspores, pollen, ovaries, ovules, embryo sacs and egg cells.

5. A part of the plant of claim 1, wherein said part of the plant is suitable for vegetative reproduction.

6. The part of the plant of claim 5, wherein said part is selected from the group consisting of cuttings, roots, stems, cells, protoplasts, leaves, meristems and buds.

7. A tissue culture of the lettuce plant of claim 1.

8. The tissue culture as claimed in claim 7, wherein said tissue culture is derived from a tissue selected from the group consisting of leaves, pollen, embryos, cotyledon, hypocotyls, meristematic cells, roots, root tips, anthers, flowers, seeds and stems.

9. A plant that has all of the morphological and physiological characteristics of lettuce cultivar 79-11 RZ, representative seed of which having been deposited under NCIMB Accession No. 41614, said plant grown from the seed as claimed in claim 2.

10. A plant that has all of the morphological and physiological characteristics of lettuce cultivar 79-11 RZ, representative seed of which having been deposited under NCIMB Accession No. 41614, said plant regenerated from the part of the plant as claimed in claim 3.

11. A plant that has all of the morphological and physiological characteristics of lettuce cultivar 79-11 RZ, representative seed of which having been deposited under NCIMB Accession No. 41614, said plant regenerated from the tissue culture as claimed in claim 7.

12. A progeny of a lettuce plant of claim 1.

13. The progeny as claimed in claim 12, wherein said progeny is produced by sexual or vegetative reproduction of said lettuce plant of claim 1 or a progeny plant thereof, and wherein the regenerated plant has all of the morphological and physiological characteristics of lettuce cultivar 79-11 RZ, representative seed of which having been deposited under NCIMB Accession No. 41614.

14. A progeny of the lettuce plant of claim 9.

15. A progeny of the lettuce plant of claim 10.

16. A progeny of the lettuce plant of claim 11.

17. A progeny of the lettuce plant of claim 1, wherein the plant has an extraordinary high number of green, round-shaped leaves as found in lettuce cultivar 79-11 RZ, representative seed of which having been deposited under NCIMB Accession No. 41614, and is modified in one or more other characteristics.

18. The progeny as claimed in claim 17, wherein the modification is effected by mutagenesis.

19. The progeny as claimed in claim 17, wherein the modification is effected by transformation with a transgene.

20. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

21. A method of producing a lettuce cultivar having an extraordinary high number of green, round-shaped leaves, an extraordinary low number of apices and resistance to downy mildew comprising: crossing a mother lettuce plant with a father lettuce plant to produce a hybrid seed; growing said hybrid seed to produce a hybrid plant; selfing said hybrid seed to produce $F_2$ progeny seed; and selecting said $F_2$-plants for having an extraordinary high leaf number.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce plant having a trait of black seeds; a trait of green, round-shaped leaves; a multileaf trait; an extraordinarily low number of apices trait; a resistance to *Bremia lactucae* Regal trait, and genetic information in its genome for expressing the black seeds trait, the green, round-shaped leaves trait, the multileaf trait, the extraordinarily low number of apices trait and the resistance to *Bremia lactucae* Regal trait,
wherein the multileaf trait is caused by a single recessive genetic factor which is present in the lettuce plant in a homozygous state whereby the lettuce plant has the multileaf trait and green, round-shaped leaves,
wherein the multileaf trait includes that (i) at harvest maturity the fresh weight of the above-ground part of the lettuce plant expressing the multileaf trait is between 200 and 300 grams, and (ii) under the same environmental conditions, at the plant stage before bolting when the above-ground dry matter is between 100 and 400 grams, the lettuce plant expressing the multileaf trait grows at least about 2 to 4 times as many leaves as another lettuce plant of the same variety that is not homozygous as to the genetic information for expressing the multileaf trait,
wherein the extraordinarily low number of apices trait includes that under warm environment conditions of between 15° C. and 25° C., the multileaf lettuce plant also expressing the extraordinarily low number of apices trait has at harvest maturity about 1 to 3 times lower number of apices than a multileaf lettuce plant at harvest maturity that does not express the extraordinarily low number of apices trait and was grown under the same warm environment conditions,
wherein the resistance to *Bremia lactucae* Regal trait includes resistance to strains B1:16, B1:17, B1:18, B1:20, B1:22, B1:23, B1:24, B1:25, B1:26, Ca-VII, Ca-VIII, NL341, and NL519, and
wherein the genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

2. A seed of the plant of claim 1.

3. A part of the plant of claim 1, wherein said part of the plant is suitable for sexual reproduction.

4. The part of the plant of claim 3, wherein said part is selected from the group consisting of microspores, pollen, ovaries, ovules, embryo sacs and egg cells.

5. A part of the plant of claim 1, wherein said part of the plant is suitable for vegetative reproduction.

6. The part of the plant of claim 5, wherein said part is selected from the group consisting of cuttings, roots, stems, cells, protoplasts, leaves, meristems and buds.

7. A tissue culture of the lettuce plant of claim 1.

8. The tissue culture as claimed in claim 7, wherein said tissue culture is derived from a tissue selected from the group consisting of leaves, pollen, embryos, cotyledon, hypocotyls, meristematic cells, roots, root tips, anthers, flowers, seeds and stems.

9. A lettuce plant that having the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614, wherein the lettuce plant is grown from the seed as claimed in claim 2.

10. A lettuce plant having the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614, wherein the lettuce plant is regenerated from the part of the plant as claimed in claim 3.

11. A lettuce plant having the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614, wherein the lettuce plant is said plant regenerated from the tissue culture as claimed in claim 7.

12. A $F_1$, $F_2$, $F_3$, $F_4$, $F_5$, $F_6$, or $F_7$ progeny of a lettuce plant of claim 1, wherein the $F_1$, $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

13. A $F_1$, $F_2$, $F_3$, $F_4$, $F_5$, $F_6$, or $F_7$ progeny of the lettuce plant of claim 9, wherein the $F_1$, $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

14. A $F_1$, $F_2$, $F_3$, $F_4$, $F_5$, $F_6$, or $F_7$ progeny of the lettuce plant of claim 10, wherein the $F_1$, $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

15. A $F_1$, $F_2$, $F_3$, $F_4$, $F_5$, $F_6$, or $F_7$ progeny of the lettuce plant of claim 11, wherein the $F_1$, $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

16. A $F_1$, $F_2$, $F_3$, $F_4$, $F_5$, $F_6$, or $F_7$ progeny of the lettuce plant of claim 1, wherein the $F_1$, $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614, and is modified in one or more other characteristics.

17. A lettuce plant of claim 1, wherein the lettuce plant is cultivar 79-11 RZ, which is also referred to as Emerson.

18. The progeny as claimed in claim 16, wherein the modification is effected by transformation with a transgene.

19. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1 or 17.

20. A method of producing a lettuce plant that has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614, said method comprising,
crossing a first lettuce plant with a second lettuce plant wherein the first or second lettuce plant is the lettuce plant of claim 1 or claim 18 or a $F_1$, $F_2$, $F_3$, $F_4$, $F_5$, $F_6$, or $F_7$ progeny of the lettuce plant of claim 1 or claim 18 having the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614,
wherein the lettuce plant produced by the method that has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614 is a second or further generation descendant of the cross.

21. A lettuce plant that is produced by the method of claim 20 that has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

22. The lettuce plant of claim 1 or 17 grown from seed deposited under NCIMB Accession No. 41614.

23. A $F_1$ progeny of a lettuce plant produced by sexual reproduction of the lettuce plant of claim 1, wherein the $F_1$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

24. A $F_2$, $F_3$, $F_4$, $F_5$, $F_6$, or $F_7$ progeny of a lettuce plant produced by sexual reproduction of a progeny plant of a lettuce plant of claim 1, wherein the $F_2$, $F_3$, $F_4$, $F_5$, $F_6$, or $F_7$ progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

25. A progeny of a lettuce plant produced by vegetative reproduction of the lettuce plant of claim 1 or a progeny plant thereof, wherein the progeny has the black seeds trait, the green, round-shaped leaves trait, the multileaf trait, the extraordinarily low number of apices trait and the resistance to *Bremia lactucae* Regal trait, and genetic information for expressing the black seeds trait, the green, round-shaped leaves trait, the multileaf trait, the extraordinarily low number of apices trait and the resistance to *Bremia lactucae* Regal trait is as found in a lettuce plant, representative seed of which having been deposited under NCIMB Accession No. 41614.

\* \* \* \* \*